United States Patent [19]

Szymanski

[11] 4,432,967
[45] Feb. 21, 1984

[54] CONTRACEPTIVE COMPOSITION

[75] Inventor: Chester D. Szymanski, Martinsville, N.J.

[73] Assignee: National Starch and Chemical Corp., Bridgewater, N.J.

[21] Appl. No.: 392,266

[22] Filed: Jun. 25, 1982

[51] Int. Cl.$^3$ ...................... A61K 31/74; A61K 31/78
[52] U.S. Cl. ........................................ 424/78; 424/81; 424/DIG. 14
[58] Field of Search .................... 424/81, 78, DIG. 14, 424/DIG. 10

[56] References Cited

U.S. PATENT DOCUMENTS 2,662,077 12/1953 Hadidian et al. ....... 424/DIG. 14 X
3,072,618 1/1963 Turbak ......................... 525/333.5 X

OTHER PUBLICATIONS

Pincus et al.-Arch. Biochem. vol. 19, 1948, pp. 388–396.
Bernfeld et al.-Arch. Biochem. & Biophys., vol. 92, 1961, pp. 232–240.
Bikales, Water–Soluble Polymers, Plennum Press, New York (Series) Polymer Sci. & Tech., vol. 2, 1973.

Primary Examiner—Leonard Schenkman
Attorney, Agent, or Firm—James & Franklin

[57] ABSTRACT

A contraceptive composition for vaginal administration which contains a salt of a sulfonated styrene polymer and a pharmaceutically acceptable carrier. Effective polymers have a degree of substitution of from about 0.7 to 1.3 and an average molecular weight of between 600 and 7,000,000.

11 Claims, No Drawings

CONTRACEPTIVE COMPOSITION

BACKGROUND OF THE INVENTION

Extensive research carried on throughout recent years in methods of human birth control has resulted in the development of various contraceptive means such as, for example, oral contraceptives, intrauterine devices (IUD), diaphragms, and vaginal chemicals adapted for vaginal insertion. Experience has shown that none of these means has been found to be fully safe and satisfactory. Oral contraceptives, for example, developed in the 1950's and commonly know as the "pill", are highly effective and widely utilized today in a world-wide basis. Nevertheless, use of the pill may result in undesirable side effects such as headaches and nausea, and infrequently may be associated with more serious systemic effects. IUD's ordinarily require trained medical help and supervision for proper insertion and maintenance, and have been reported to cause internal bleeding.

Among the most commonly used vaginal chemicals are the spermicidal agents, for example, physiologically acceptable mono(alkylphenyl) ethers of polyethylene glycols wherein the alkyl group preferably contains from 1 to 10 carbon atoms and the polyethylene glycol preferably contains from 2 to 12 ethyleneoxy units, such as nonoxynol-9. These contraceptive agents, which are very often utilized with a diaphragm or other contraceptive device for added contraceptive protection, effectively kill the mammalian spermatozoa thereby preventing the fertilization of the egg. Most often these chemicals are prepared in the form of creams, jellies, suppositories, foams and foaming tablets which are intended to be introduced into the vagina just prior to intercourse.

Considering the above-noted deficiencies as representative, it becomes apprent that in order for any means of providing contraception or birth control to be widely accepted, it must be effective, safe on a short and long term basis, preferably inexpensive and convenient to use.

It is thus an object of this invention is to provide a contraceptive composition for vaginal administration which composition is contraceptively effective for relatively prolonged periods of time after its administration.

SUMMARY OF THE INVENTION

This invention relates to a contraceptive composition intended for vaginal administration. The invention also relates to a method of controlling fertility in warm blooded female animals by vaginal administration of the contraceptive composition described herein. The contraceptive compositions of the present invention possess an advantage over known vaginal contraceptives in that the compositions herein have a prolonged contraceptive physiological effect and need not be inserted into the vagina immediately prior to intercourse.

I have discovered that certain sulfonated styrene polymers (in salt form) when vaginally administered to a female animal prior to mating provide the animal with effective contraceptive activity which otherwise would result in pregnancy. According to the present invention, therefore, there is provided for vaginal administration a contraceptive composition containing a polymer having sulfonated styrene mers of the following structure:

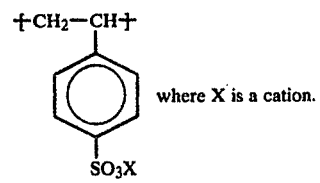

where X is a cation.

The polymer may be sulfonated polystryrene or a copolymer of styrene wherein sulfonated styrene and another compatible comonomer forms the backbone of the polymer. Suitable comonomers for incorporation in forming the useful copolymers herein are any ethylenically unsaturated monomers copolymerizable with the styrene monomer and include, for example, maleic anhydride, methacrylic acid, acrylic acid, methyl methacrylate, p-vinyl toluene and alpha-methyl styrene. The amount of comonomer employed would ordinarily be no more than about one-third of the final styrene polymer, and use of the sulfonated polystyrene (homopolymer) is preferred, since the contraceptive activity is believed to stem from the sulfonated sytrene mer. The sulfonated polymers are used in the salt form with the cation being any common cation, for example, sodium, potassium, ammonium, tetramethyl ammonium, calcium, aluminum and the like. Effective polymers have a degree of substitution (D.S.) with respect to the sulfonate group of from about 0.7 to 1.3, and an average molecular weight of between about 600 and 7,000,000. In practice of this invention, however, it is preferred that the sulfonated polymer of the contraceptive composition be in the form of the sodium salt because of its biological compatibility, and have a D.S. of about 0.9 and an average molecular weight of about 3,000 to 1,000,000. Sulfonated polystyrene polymers having an average molecular weight of from about 70,000 to 500,000 are most preferred. While precise demarcation is not clear, testing data indicates that strongest contraceptive activity is found in polymers having an average molecular weight of from about 70,000 to about 500,000. Below 70,000 and above 500,000 as the molecular weight of the polymers increases and reaches 6–7,000,000 contraceptive activity is gradually reduced.

The contraceptive compositions of the present invention are prepared by blending and dispersing the sulfonated polymer into a pharmaceutically acceptable carrier (vehicle) such as an oleaginous, aqueous or particulate solid base depending on the desired final form of the composition. The proportion of sulfonated polymer with respect to the carrier (which is physiologically acceptable) can be determined with respect to a particular unit dosage as at least that amount which effectively inhibits conception in the treated female. It can be understood that the proportion of sulfonated polymer is somewhat affected by its solubility and rate of release from a particular vehicle used in forming specific dosage units. Most of the compositions herein will be formulated to contain from about 0.1 to 20% by weight of the sulfonated polymer. Selection of the actual concentration of sulfonated polymer needed in a given vehicle for a specific application can be easily determined by the skilled practitioner. Optionally, the contraceptive composition may include a known spermicide.

In a further aspect, the invention relates to a method of controlling fertility by providing contraceptive protection (inhibiting conception) to warm blooded female animals by vaginal administration of the contraceptive composition described herein in unit dosage form. A significantly high proportion of females thus treated will not become pregnant despite mating or intercourse during several hours after administration of the contraceptive composition.

DESCRIPTION OF THE PREFERRED EMBODIMENTS

With regard to the preparation of the sulfonated polystyrene and sulfonated styrene copolymer, the base polymer is first polymerized by any conventional polymerization method, e.g. a bulk suspension, solution or emulsion method, and the sulfonation of the base polymer may be carried out, for example, according to the method taught in U.S. Pat. No. 3,072,618 to Turbak, using phosphorous compound-sulfur trioxide adducts, which patent by reference is incorporated herein. Alternatively, the sulfonated monomer can be polymerized to form the active sulfonated polymer directly with limitations familiar to those skilled in the art of polymer chemistry.

By selection of the appropriate pharmaceutical carrier, the compositions of the invention may take a variety of forms including semisolids formulations such as vaginal creams, creams to coat diaphragms or condoms, jellies, foams, aerosols or the like, as well as solids formulations which tend to soften or melt at body temperature or disintegrate on contact with moisture. Solid compositions include vaginal suppositories or tablets, e.g., polyethylene glycol or glycerine based suppositories, gel-forming tablets or effervescent tablets and suppositories.

Suitable cream formulations are prepared using water-in-oil or oil-in-water emulsions. The emulsion may contain oils which are commonly used in pharmaceutical preparations, e.g., vegetable oils such as peanut oil or olive oil or fatty acids, fatty alcohols and esters thereof. These creams may also contain conventional emulsifying agents, such as monoglycerides, alginates, fatty acid esters of sorbitol or ethyoxylated derivatives thereof and/or thickening agents. Foams and aerosols additionally contain physiologically acceptable conventional propelling agents such as chlorofluoromethane or chlorofluoroethane.

Jellies are prepared using an aqueous base and gel-forming and thickening ingredient. Preferred gel-forming agents are cellulose derivatives, for example, cellulose ethers, especially methyl or ethyl cellulose or carboxymethyl cellulose. Other gel-forming and thickening ingredients are vegetable gums which are stable at pH values between about 4 and 9, preferably gum tragacanth or acacia, polyvinyl alcohol, high molecular weight sulfonated styrene polymers, etc.

Other forms of administering the polymer salts include so-called "slow release" or depot formulations where the active ingredient will operate over relatively extended periods of time.

Additionally adjuvants which may be incorporated into these formulations are hygroscopic agents, such as glycerine or propylene glycol, physiologically acceptable buffer compositions, e.g. phosphate buffers, anti-molding agents, such as p-hydroxybenzoic acid, lower alkyl esters (e.g., methylparaben or propylparaben), or sorbic acid, antiseptic agents, such as boric acid, cresols, chlorinated phenols, or organomercuric salts, e.g., phenylmercuric acetate, antioxidants, perfumes, etc. Solid vaginal tablets may contain solid gel-forming carriers, e.g., the above-mentioned gel-forming agents, other water-soluble and/or hygroscopic conventional pharmaceutical solids carriers like lactose, or polyvinyl pyrrolidone, and may also comprise the above-mentioned adjuvants and conventional tabletting-adjuvants such as binder or lubricants. Suppositories may contain polyethylene glycols which are solids at normal temperatures, e.g., mixtures of polyethylene glycol 6000 (15 to 40%), polyethylene glycol 1540 (9 to 26%) and polyethylene glycol 400 (6 to 18%), carbowaxes, and glycerin, optionally in admixture with pharmaceutically acceptable fats and emulsifying agents and the above-mentioned adjuvants. Vaginal suppositories may also be in the form of soft gelatin capsules containing a liquid or semi-liquid water-soluble carrier material such as carboxymethylcellulose gels and glycerin into which an amount of from about 5 to 500 mg. of a salt of the sulfonated polymer are incorporated. Preferably, the compositions are buffered to vaginal pH-values, that is, to a pH-value between about 4.5 and about 5; but higher pH-values up to about 7.5 are also acceptable. Effervescent suppositories or tablets further contain ingredients which will release an inert gas upon contact with moisture, e.g., mixtures of $NaHCO_3$ and $Na_2HPO_4$ which will form carbon dioxide.

The following examples will illustrate the invention is several embodiments.

EXAMPLE I

The in vivo contraceptive activity of the compositions herein prepared using a variety of sulfonated polymer salts was tested according to the following procedure. Each of the polymer salts to be tested was formulated into a jelly composition at a concentration of 5, 25 and 50 mg/ml concentration by combining the salt and K-Y Jelly (commercially available). Two polymeric salts were tested only at the 50 mg/ml concentration. Each formulation at each concentration was administered to 5 or 10 rabbits by inserting 1.01 ml of the jelly formulation well into the vagina of the rabbit several minutes prior to mating with a proven fertile male rabbit.

The rabbits were then mated and the percent pregnancy and number of implants were evaluated for each test rabbit. A control wherein no contraceptive was employed and a vehicle control wherein only the K-Y Jelly was inserted into the vagina were used as a comparison. After mating the female test rabbits were sacraficed on day 15 of gestation and the number of pregnancies and implants was recorded. The results are indicated in Table I.

TABLE I

| Polymer | Conc. of Polymer in Jelly (mg/ml) | Pregnancy (%)* | Implants (Mean + Std. Error) |
|---|---|---|---|
| 1. Control | 0 | 100 | 9.0 ± 1.0 |
| 2. Vehicle Control | 0 | 80 | 7.2 ± 2.0 |
| 3. Sodium salt of polystyrene (M.W. 500,000; essentially linear) | 5 | 50** | 2.6 ± 1.1 |
| | 25 | 30** | 2.9 ± 1.5 |
| | 50 | 0** | 0 |
| 4. Sodium salt of sulfonated polystyrene (M.W. 500,000; essentially linear) dialyzed and precipitated from acetone | 5 | 20 | 0.8 ± 0.8 |
| | 25 | 0 | 0 |
| | 50 | 20 | 2.4 ± 2.4 |
| 5. Sodium salt of sulfonated polystyrene (M.W. 400,000; linear) | 5 | 20 | 1.2 ± 1.2 |
| | 25 | 20 | 3.0 ± 3.0 |
| | 50 | 0 | 0 |

TABLE I-continued

| Polymer | Conc. of Polymer in Jelly (mg/ml) | Pregnancy (%)* | Implants (Mean + Std. Error) |
|---|---|---|---|
| 6. Sodium salt of sulfonated polystyrene (M.W. 70,000; linear) | 5<br>25<br>50 | 80<br>40<br>0 | 8.8 ± 2.2<br>2.0 ± 1.8<br>0 |
| 7. Sulfonated styrene-maleic anhydride copolymer sodium salt (M.W. 3000) | 5<br>25<br>50 | 100<br>20<br>20 | 6.6 ± 1.0<br>2.2 ± 2.2<br>0.2 ± 0.2 |
| 8. Sodium salt of sulfonated polystyrene (M.W. 7,000,000; linear) | 50 | 60 | 5.4 ± 2.9 |
| 9. Sodium salt of sulfonated polystyrene (M.W. 6-7,000,000; crosslinked with xylene dichloride) | 50 | 80 | 4.8 ± 2.4 |
| 10. Sulfonated 70/30 styrene/methyl methacrylate copolymer, sodium salt (M.W. apx. 500,000) | 5<br>25<br>50 | 60<br>40<br>0 | 4.0 ± 1.7<br>1.6 ± 1.4<br>0 |
| 11. Sulfonated 93/7 styrene/methacrylic acid copolymer, sodium salt (M.W. apx. 60,000) | 5<br>25 | 40<br>60 | 3.4 ± 2.1<br>6.2 ± 2.7 |
| 12. Sulfonated 93/7 styrene/methacrylic acid copolymer, sodium salt (M.W. apx. 60,000) dialyzed and freezedried | 50 | 20 | 1.0 ± 1.0 |

*Five rabbits were used for each test except where indicated.
**Ten rabbits were used.

EXAMPLE II

This example illustrates the contraceptive effectiveness of a representative composition of this invention for a prolonged period of time after introduction thereof into the vagina.

Polymer 3 of Example I, formulated using K-Y Jelly into a jelly composition, was administered at a concentration of 50 mg/ml to 5 or 10 rabbits by inserting 1.0 ml of the jelly formulation well into the vagina of the rabbit. A given period of time was allowed to lapse between administration and mating with a proven fertile male rabbit. After mating, the percent pregnancy and number of implants were evaluated for each test rabbit. The results are given in Table II.

TABLE II

| Interval between Adminstration and Mating (hours) | Pregnancy (%)* | Implants (Mean + Std. Error) |
|---|---|---|
| 0 | 0 | 0 |
| 1 | 0 | 0 |
| 4 | 0** | 0 |
| 5 | 20 | 0.2 ± 0.2 |
| 6 | 0 | 0 |
| 7 | 40 | 4.6 ± 2.9 |
| 8 | 20** | 1.2 ± 1.2 |
| 24 | 80 | 6.2 ± 2.4 |

Five rabbits were used for each test except where indicated.
**Ten rabbits were used.

It can be seen that the percent pregnancy does not significantly increase even when mating takes place several hours after administration of the composition of this invention.

EXAMPLE III

This example illustrates a typical preparation of a vaginal suppository of the invention incorporating a sodium salt of sulfonated polystyrene homopolymer. The needed ingredients are:

| | parts per hundred |
|---|---|
| polyethylene glycol 1000 | 91 |
| polyethylene glycol 300 | 2 |
| methyl cellulose | 2 |
| sulfonated polystyrene, sodium salt (MW 500,000) | 5 |

The polyethylene glycol 1000 is melted and blended with the polyethylene glycol 300 at a temperature of 66° to 70° C. The methyl cellulose and sulfonated polystyrene are thereafter dispersed in the warm mixture using slow speed agitation until the ingredients are thoroughly mixed. The mixture is cooled to about 55° C. and poured into chilled oviform shaped molds. The molds are thereafter placed in a freezer for about 2 hours after which the suppositories are removed and ready for use or wrapping and storage.

EXAMPLE IV

This example illustrates an additional preparation of a vaginal suppository incorporating a salt of a sulfonated copolymer of styrene and maleic anhydride (90/10%, by weight) which also includes a known spermicide.

| | parts per hundred |
|---|---|
| polyethylene glycol 1000 | 80 |
| polyethylene glycol 4000 | 12 |
| polyethylene glycol 300 | 2 |
| nonoxynol-9 | 1 |
| sulfonated copolymer of styrene/maleic anhydride sodium salt (MW 3,000) | 5 |

The solid polyethylene glycol ingredients are melted at a temperature of about 66° to 70° C. and the polyethylene glycol 300 is added thereto. The styrene copolymer and nonoxynol-9 are dispersed in the warm mixture using slow speed agitation until the ingredients are thoroughly mixed. The mixture is cooled to about 55° C. and the procedure of Example III is followed to produce the finished suppositories.

In summary, the invention is seen to provide a contraceptive composition for vaginal administration which is convenient to use and is contraceptively effective for relatively prolonged periods of time after is administration.

Variations may be made in the procedure and proportions without departing from the scope of this invention as defined by the appended claims.

What is claimed is:

1. A contraceptive composition for vaginal administration which comprises an effective amount of a salt of a sulfonated homo- or copolymer of styrene and a pharmaceutically acceptable carrier, said composition being in the form of a cream, foam, jelly or suppository.

2. The composition of claim 1 wherein the sulfonated polymer is the sodium salt of a sulfonated styrene polymer having an average molecular weight of from about 3,000 to 1,000,000 and a D.S. of from about 0.7 to 1.3 and is present in an amount of about 0.1 to 20% by weight of the composition.

3. The composition of claim 2 wherein the sulfonated polymer is sulfonated polystyrene and has an average molecular weight of from about 70,000 to 500,000 and a D.S. of about 0.9.

4. The composition of claim 2 wherein the polymer is a salt of a sulfonated copolymer of styrene and maleic anhydride.

5. The composition of claim 2 wherein the polymer is a salt of a sulfonated copolymer of styrene and methacrylic acid.

6. The composition of claim 2 wherein the polymer is a salt of a sulfonated copolymer of styrene and methyl methacrylate.

7. The composition of claim 3 wherein the composition includes the spermicide nonoxynol-9.

8. A method of inhibiting conception in a warm-blooded female animal comprising the step of introducing and maintaining within the vagina of such animal an effective amount of a contraceptive composition which comprises a salt of a sulfonated homo- or copolymer of styrene and a pharmaceutically acceptable carrier.

9. The method of claim 8 wherein the sulfonated polymer is the sodium salt of a sulfonated styrene polymer having an average molecular weight of from about 3,000 to 1,000,000 and a D.S. of from about 0.7 to 1.3 and is present in an amount of about 0.1 to 20% by weight of the composition.

10. The method of claim 9 wherein the sulfonated polymer is sulfonated polystyrene and has an average molecular weight of from about 70,000 to 500,000 and a D.S. of about 0.9.

11. The method of claim 9 wherein the composition is in a form of a cream or jelly or suppository.

* * * * *